United States Patent [19]

Noble

[11] Patent Number: 4,852,641

[45] Date of Patent: Aug. 1, 1989

[54] PLASMA BAG SUPPORT RACK

[76] Inventor: Bradley T. Noble, 110 S. Helberta Ave., Redondo Beach, Calif. 90277

[21] Appl. No.: 161,720

[22] Filed: Feb. 29, 1988

[51] Int. Cl.$^4$ ............................................... F28F 7/00
[52] U.S. Cl. .................................... 165/80.1; 422/307; 422/25; 422/41
[58] Field of Search .................. 165/80.1, 80 G, 80 R, 165/104.19, 46; 604/408; 248/95, 99; 422/300, 307, 99, 25, 40, 41, 301

[56] References Cited

U.S. PATENT DOCUMENTS

| | | | |
|---|---|---|---|
| 2,061,427 | 11/1936 | King | 165/46 X |
| 2,914,445 | 11/1959 | Clarke | 165/104.19 X |
| 4,486,389 | 12/1984 | Darnell et al. | 165/46 X |

Primary Examiner—Larry Jones

[57] ABSTRACT

A plasma bag support rack is described which is useful for suspending frozen plasma bags in a water bath. The support rack includes a main cross member that has two pairs of vertically oriented hooks projecting downward. The cross member has rubber coated ends to prevent slippage during thawing. Frozen plasma bags are suspended by the support rack hooks from the support holes at the top of the bags. The rubber coated cross member ends are then seated on the top edge of a water bath during plasma bag thawing. The support rack holds the entry ports of frozen plasma bags out of the bacteria contaminated water which is commonly found in plasma thawing water baths. This support rack provides a means for safe and rapid thawing of frozen plasma bags.

12 Claims, 2 Drawing Sheets

PLASMA BAG SUPPORT RACK

FIELD OF THE INVENTION

This invention relates to a support rack for suspending frozen bags of human plasma during thawing in a water bath.

BACKGROUND OF THE INVENTION

Plastic bags to store frozen human plasma have been employed by blood collection centers, hospitals and other medical facilities for many years. These bags of frozen plasma are stored until they are ready for use. The plasma is generally thawed in a water bath prior to transfusion.

Plastic bags used for this purpose typically comprise two sheets of heavy plastic which have been sealed together at their edges. At the top edge of the bag there is a flap formed by the two sheets being sealed together. Typically there are entry ports or openings at the top of the bag which communicate with the interior cavity of the bag. There are normally at least two support holes at the top of the plasma bag which would allow the bag to be suspended by the plasma bag support rack hooks.

During the thawing process it is essential that the entry port openings at the top of the bag do not come in contact with the water in the water bath. This is due to the frequent contamination of the water baths with pathogenic bacteria. It has been documented in medical literature that if the entry ports come into contact with the contaminated water, the patient can still become infected even after the entry ports have been dried with clean gauze.

To minimize the possibility of contamination of the entry ports of the plasma bag with bacteria laden water, plasma overwrap bags are commonly used. Overwrap bags are made of thin plastic and are designed to place frozen plasma bags into during thawing. These bags have their problems, however, as they delay the thawing process and they also frequently leak allowing contamination to occur.

Some water baths come equipped with metal baskets which support the bottom and the sides of the plasma bag, but not the top of the bag. As a result the entry ports of the plasma bag can fold over and come in contact with the contaminated water.

There has not heretofore been provided a plasma bag support system having the advantages inherent in the system of the present invention.

SUMMARY OF THE INVENTION

The present invention is directed to a rack extending the width of a water bath. Plasma bags can be attached to this rack to support the top of the bags during thawing. The plasma bag is first placed into a plastic overwrap bag and immersed in the water bag for several minutes. This step prevents bag cracking due to the rapid temperature change. Next the plasma bag support holes are penetrably engaged by the support rack hooks. The support rack and suspended plasma bags are then placed across the width of the water bath. The entry ports on the plasma bags are held safely above the contaminated water during thawing.

The plasma bag support system of this invention is particularly desirable for two reasons. It supports the plasma bag in a way that prevents bacteria contaminated water from contacting the entry port area of the bag. It also does not delay the thawing process as do the plastic overwrap bags. The support system of the invention comprises:

(a) A support rack having a cross member that extends the width of and rests on the top edge of a water bath.

(b) Spaced apart and vertically oriented hooks that project downward from said cross member as a means for suspending frozen plasma bags.

(c) Rubber coated cross member ends to prevent slippage of the rack.

It is therefore a primary object of the present invention to provide a rack for suspending frozen plasma bags in a water bath.

Another object of the present invention is to provide a cross member extending across the cavity of a water bath for suspending within the water bath frozen plasma bags.

A further object of the present invention is to provide a rack which is readily attachable to and detachable from a water bath for freely suspending frozen plasma bags within the water bath.

Yet another object of the present invention is to provide a method for suspending fozen plasma bags within a water bath.

These and other objects of the present invention will become apparent to those skilled in the art as the description thereof proceeds.

DESCRIPTION OF THE PREFERRED EMBODIMENT

Figure 1:
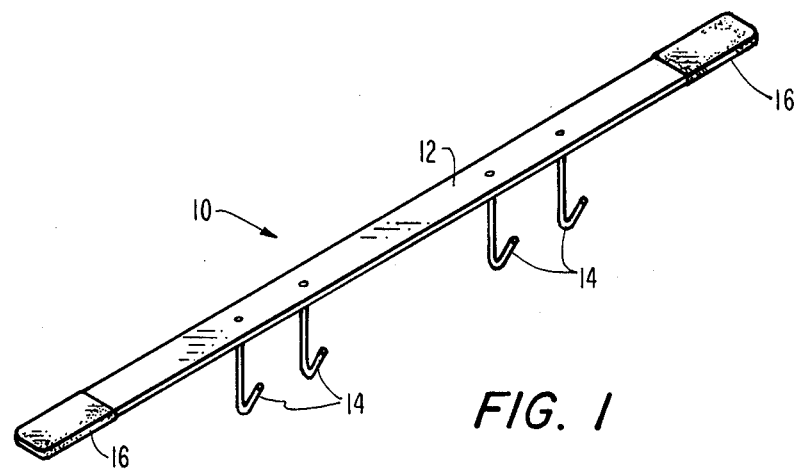
FIG. 1 is an isometric view of the rack.

Referring to FIG. 1 there is illustrated a rack 10 for suspending frozen plasma bags in a water bath. The rack has a long cross member 12 and two pairs of vertically oriented hooks 14. The cross member 12 and hooks 14 may be manufactured from non-corrosive metals such a aluminum and brass. The cross member ends 16 are coated with rubber to prevent slippage.

Figure 2:
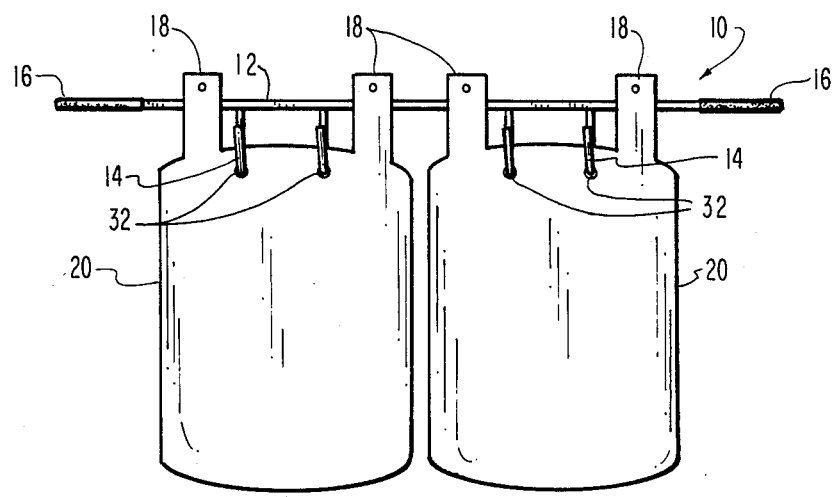
FIG. 2 is a front view of two frozen plasma bags suspended from the rack.

Attention is directed to FIG. 2 showing two frozen plasma bags 20 suspended from the rack 10. The vertically oriented hooks 14 of the rack 10 penetrably engage with the support holes 32 of the plasma bags 20. The hooks 14 are spaced apart a distance approximately equal to the distance between the support holes 32 in the plasma bags 20.

Figure 3:
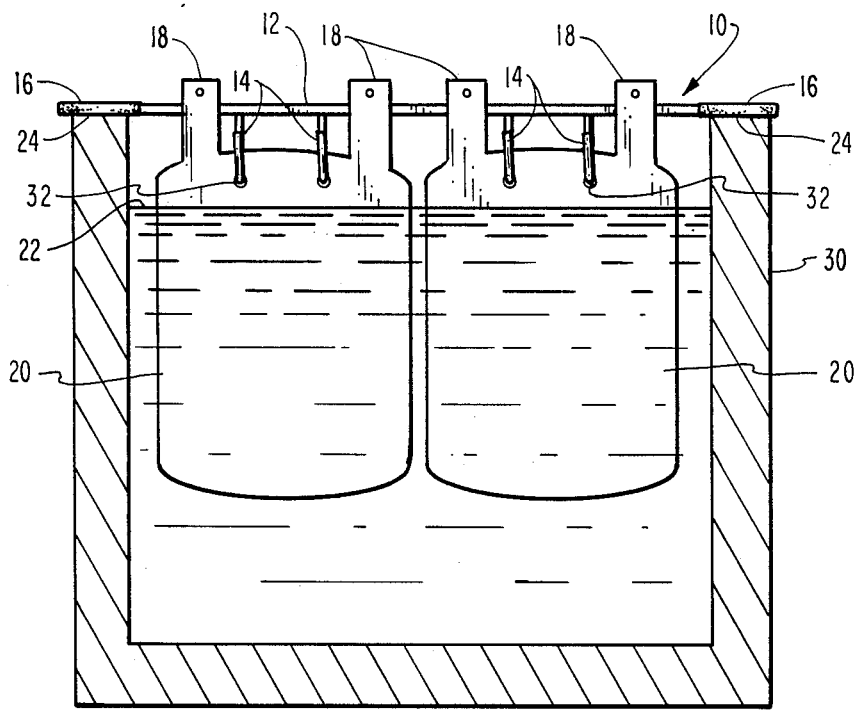
FIG. 3 is a partial cross sectional view illustrating two frozen plasma bags within a water bath and suspended from the rack.

In FIG. 3 a cross section of a water bath 30 is shown. The rack 10 is shown suspending frozen plasma bags 20 in the cavity of the water bath 30. The rubber coated ends 16 of the rack 10 rest on the top edge 24 of the water bath 30. The plasma bag entry ports 18 are held above the water level 22 by the vertically oriented hooks 14 of the rack 10.

Figure 4:
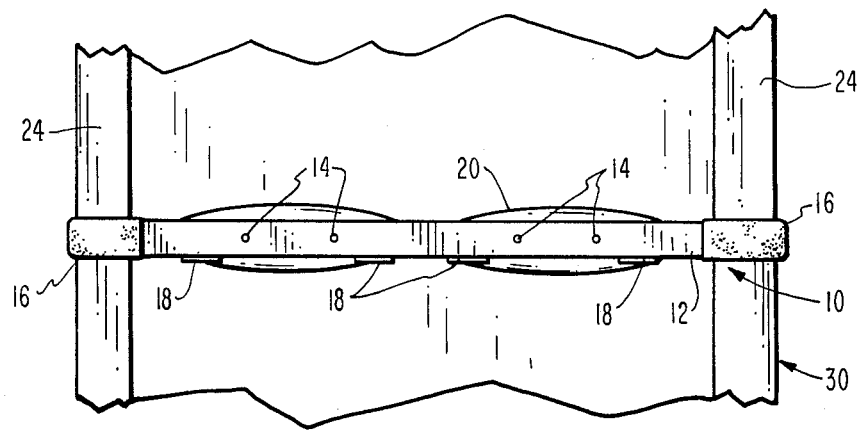
FIG. 4 is a top view cutaway portion of a water bath having two frozen plasma bags suspended from the rack.

Referring to FIG. 4 which is a top view cutaway portion of the water bath 30. The rack 10 is shown extending the width of the water bath 30. The frozen plasma bags 20 are shown suspended by the hooks 14 of the rack 10. The rubber coated ends 16 are shown resting on the top edge 24 of the water bath 30 to prevent slippage.

In operation after thawing is completed the rack 10 supporting the now thawed plasma bags 20 may be manually lifted out of the water bath 30. The thawed plasma bags 20 may then be removed from the hooks 14 of the rack 10 and dried with a towel. The thawed plasma bag 20 is then free from water contamination in the entry ports 18 and is ready for transfusion.

While the principles of the invention have now been made clear in illustrative embodiment, there will be immediately obvious to those skilled in the art many modifications of structure, arrangement, proportions, elements, materials and components, used in the practice of the invention which are particularly adapted for specific environments and operating requirements without departing from those principles.

I claim:

1. A plasma bag support rack particularly configured for suspending within a conventional water bath frozen plasma bags of the type having at least two support holes at the top of the plasma bag, said support rack comprising in combination:
   a. a support rack having a cross member that extends the width of and rests on the top edge of a water bath ; and
   b. spaced apart and vertically oriented pairs of hooks that project downward from the cross member as a suspending means for frozen plasma bags ; and
   c. rubber coated cross member ends to prevent slippage of the rack.

2. The rack as set forth in claim 1 wherein the water bath includes a top edge wherein each end of said support rack includes a means for seating on the top edge of the water bath.

3. The rack as set forth in claim 2 wherein the ends of the support rack are planar .

4. The rack as set forth in claim 2 wherein said support rack includes rubber coated ends for seating and gripping the top edge of said water bath.

5. The rack as set forth in claim 1 wherein said suspending means includes one or more (two) pairs of spaced apart hooks.

6. A rack as set forth in claim 1 wherein the spaced apart pairs of hooks penetrably engage the support holes at the top of the frozen plasma bag as a means for holding the plasma bag upright.

7. A method for suspending frozen plasma bags in a water bath having an upper edge, said method comprising the steps of:
   a. suspending the frozen plasma bags from the support rack ; and
   b. locating the rack suspending the plasma bags on the top edge of a water bath ; and
   c. supporting the entry ports of the plasma bags during thawing to prevent their contact with the contaminated water.

8. The method as set forth in claim 7 wherein the step of suspending includes penetrably engaging the support holes at the upper end of the frozen plasma bags.

9. The method as set forth in claim 7 wherein the upper edge of the water bath includes a flat surface and wherein the step of locating includes seating the rack upon the edge of a water bath.

10. A method as set forth in claim 7 wherein said plasma bags attached to said rack are placed into the water bath as a unit .

11. A method as set forth in claim 7 wherein the entry ports of said plasma bags are maintained above the water level of the water bath by the rack during thawing.

12. A method as set forth in claim 7 wherein the plasma bags attached to said rack are removed from the water bath as a unit .

* * * * *